(12) United States Patent  
Erlich

(10) Patent No.: US 12,406,187 B2  
(45) Date of Patent: Sep. 2, 2025

(54) METHODS AND SYSTEMS FOR EMBRYO CLASSIFICATION USING MORPHO-KINETIC SIGNATURES

(71) Applicant: FAIRTILITY LTD., Madshimim (IL)

(72) Inventor: Itay Erlich, Mevo Horon (IL)

(73) Assignee: FAIRTILITY, LTD., Madshimim (IL)

( * ) Notice: Subject to any disclaimer, the term of this patent is extended or adjusted under 35 U.S.C. 154(b) by 423 days.

(21) Appl. No.: 17/785,311

(22) PCT Filed: Jan. 20, 2021

(86) PCT No.: PCT/IB2021/050420  
§ 371 (c)(1),  
(2) Date: Jun. 14, 2022

(87) PCT Pub. No.: WO2021/148961  
PCT Pub. Date: Jul. 29, 2021

(65) Prior Publication Data  
US 2023/0028645 A1    Jan. 26, 2023

Related U.S. Application Data

(60) Provisional application No. 63/036,612, filed on Jun. 9, 2020, provisional application No. 62/963,795, filed on Jan. 21, 2020.

(51) Int. Cl.  
*G06N 3/045* (2023.01)  
*G06F 18/2413* (2023.01)  
(Continued)

(52) U.S. Cl.  
CPC ....... *G06N 3/084* (2013.01); *G06F 18/24133* (2023.01); *G06N 3/045* (2023.01);  
(Continued)

(58) Field of Classification Search  
CPC . A61B 17/435; A61D 19/00; G06F 18/24133; G06N 20/10; G06N 20/20;  
(Continued)

(56) References Cited

U.S. PATENT DOCUMENTS 10,510,143 B1    12/2019    Zhou et al.  
10,942,170 B2 *    3/2021    Tan ..................... G01N 15/1433  
(Continued)

FOREIGN PATENT DOCUMENTS

WO    WO-2020001914 A1 *    1/2020    ........... G06T 3/4046  
WO    2020058931 A1    3/2020

OTHER PUBLICATIONS

International Search Report and Written Opinion issued in PCT Patent Application No. PCT/IB2021/050420, dated May 21, 2021.  
(Continued)

*Primary Examiner* — Tsung Yin Tsai  
(74) *Attorney, Agent, or Firm* — Pillsbury Winthrop Shaw Pittman LLP

(57) ABSTRACT

Methods and systems are described for improvements in embryo selection. These improvements are achieved by analyzing a series of images of a developing embryo (e.g., time-lapse images) as opposed to a single static image. For example, due to the difficulty in identifying clear distinctions between morphological states based on static images as well as the unpredictability of morpho-kinetic development of an embryo, the system analyzes the development of an embryo as a whole over a given time frame (e.g., fertilization to blastulation), which provides a better prediction of the viability of a given embryo. The analysis may take the form of a morpho-kinetic signature, which itself may be used for classifying embryos.

28 Claims, 9 Drawing Sheets

(51) Int. Cl.

| | |
|---|---|
| *G06N 3/084* | (2023.01) |
| *G06N 7/01* | (2023.01) |
| *G06T 7/00* | (2017.01) |
| *G06V 10/82* | (2022.01) |
| *G06V 20/69* | (2022.01) |
| *G16H 50/20* | (2018.01) |
| *A61B 17/435* | (2006.01) |
| *A61D 19/00* | (2006.01) |

(52) U.S. Cl.
CPC .............. *G06N 7/01* (2023.01); *G06T 7/0012* (2013.01); *G06V 10/82* (2022.01); *G06V 20/69* (2022.01); *G06V 20/698* (2022.01); *G16H 50/20* (2018.01); *A61B 17/435* (2013.01); *A61D 19/00* (2013.01); *G06T 2207/30044* (2013.01)

(58) Field of Classification Search
CPC .......... G06N 3/045; G06N 3/084; G06N 5/01; G06N 7/01; G06T 2207/30044; G06T 7/0012; G06V 10/82; G06V 20/69; G06V 20/698; G16H 50/20
See application file for complete search history.

(56) References Cited

U.S. PATENT DOCUMENTS

| | | | |
|---|---|---|---|
| 2010/0331611 A1 | 12/2010 | Konje | |
| 2014/0087415 A1 | 3/2014 | Ramsing et al. | |
| 2014/0128667 A1* | 5/2014 | Ramsing ................ | C12M 21/06 702/19 |
| 2014/0220618 A1 | 8/2014 | Wirka et al. | |
| 2014/0349334 A1* | 11/2014 | Chavez .............. | G01N 33/4833 435/34 |
| 2015/0268227 A1 | 9/2015 | Tan | |
| 2016/0078275 A1 | 3/2016 | Wang | |
| 2020/0320708 A1 | 10/2020 | Ma et al. | |
| 2021/0249135 A1* | 8/2021 | Rimestad .................. | G06T 7/33 |
| 2021/0390697 A1* | 12/2021 | Marder Gilboa ... | G06F 18/2413 |
| 2022/0392062 A1 | 12/2022 | Chavez Badiola | |
| 2023/0028645 A1* | 1/2023 | Erlich ................... | G06T 7/0012 |

OTHER PUBLICATIONS

Yoav, Kan-Tor et al.: "Automated Evaluation of Human Embryo Blastulation and Implantation Potential using Deep-Learning", Advanced Intelligent Systems, Jul. 1, 2020 (Jul. 1, 2020), vol. 2, Iss. 10, pp. 1-12.

International Preliminary Report on Patentability and Written Opinion issued in PCT Patent Application No. PCT/IB/050420, dated Aug. 4, 2022.

International Preliminary Report on Patentability and Written Opinion issued in PCT Patent Application No. PCT/IB/050421, dated Aug. 4, 2022.

Lau et al. 2019, "Embryo staging with weakly-supervised region selection and dynamically-decoded predictions," https://doi.org/10.48550/arXiv.1904.04419.

Silva-Rodrfguez et al. 2019, "Predicting the Success of Blastocyst Implantation from Morphokinetic Parameters Estimated through CNNs and Sum of Absolute Differences," 2019 27th European Signal Processing Conference (EU SIPCO), A Coruna, Spain, 2019, pp. 1-5, doi: 10.23919/EUSIPCO.2019.8902520.

Non-Final Office Action issued in related U.S. Appl. No. 17/786,878, dated Nov. 4, 2024.

* cited by examiner

METHODS AND SYSTEMS FOR EMBRYO CLASSIFICATION USING MORPHO-KINETIC SIGNATURES

This application is the U.S. national phase entry of PCT Patent Application No. PCT/IB2021/050420, which was filed on Jan. 20, 2021, which claims priority to and the benefit of U.S. Provisional Patent Application No. 63/036,612, filed on Jun. 9, 2020, and U.S. Provisional Patent Application No. 62/963,795, filed on Jan. 21, 2020, the contents of which are incorporated herein by reference in their entirety.

FIELD OF THE INVENTION

The invention relates to methods and systems for embryo classification using morpho-kinetic signatures.

BACKGROUND

In recent years, there have been several advancements in treatments for infertility. Among these treatments are in-vitro-fertilization ("IVF"). IVF involves the fertilization of an egg outside the body of a woman. The fertilized egg, once determined to be viable embryo, is then implanted back into the woman Prior to implantation, multiple tests and analysis may be performed on the embryo in order to assess viability. Such tests may include preimplantation genetic diagnosis ("PGD") and preimplantation genetic screening ("PGS"). The embryo may also undergo a manual analysis of its morphological and morpho-kinetic parameters based on images of the embryo in order to ensure the embryo is developing. For example, incubators exist that may image embryos during their development while maintaining optimal culture conditions. Embryologist may then evaluate the embryo's development based on its morphological properties at a single time point in the image. Nonetheless, properly selecting an embryo for implantation remains a difficult task.

SUMMARY

Methods and systems are described herein for improvements in embryo selection as well as other classifications of embryos. These improvements are achieved by analyzing a series of images of a developing embryo (e.g., time-lapse images) as opposed to a single static image. For example, due to the difficulty in identifying clear distinctions between morphological states based on static images as well as the unpredictability of morpho-kinetic development of an embryo, the system analyzes the development of an embryo as a whole over a given time frame (e.g., fertilization to blastulation), which provides a better prediction of the viability of a given embryo (or other classifications). For example, the presence of different visual indicators (e.g., corresponding to different morpho-kinetic events) successfully appearing within a series of respective periods of time provides a better predictor of the viability of the embryo than the presence of a single visual indicator (e.g., a single morphological feature) at a single time period because the series of visual indicators allows for the analysis of the growth rate of the embryo as well as an assessment of the trajectory of development. Additionally, for each of these images, the system may assign a probability (e.g., expressed as a float value) that the given image corresponds to the appearance of a particular visual indicator (e.g., corresponding to the embryo entering a new developmental state). As the system analyzes a series of images, the individual morpho-kinetic events result in a profile of the different morpho-kinetic events over the development of the embryo. The system may then analyze these resulting profiles of morpho-kinetic events, which act as a morpho-kinetic signature of the development of the embryo.

To recognize the appearance of different visual indicators and to correctly assess the morpho-kinetic signatures, the system may use a deep learning model that has been trained on annotated data. The annotated data may comprise static images at different development stages. The trained deep learning model may then assess the morpho-kinetic event for each image in a series of images for an embryo. The assessment may be represented as a float-point number in a vector, which in some embodiments, may correspond to a likelihood that the embryo has reached the given development stage. Furthermore, as the trained deep learning model has provided a probability and/or morpho-kinetic event for each image in a set of images, the system can generate morpho-kinetic signature that is a representation of the morpho-kinetic events in the embryo as a function of time. This morpho-kinetic signature may be represented numerically (e.g., as vector array) or visually.

The morpho-kinetic signature itself may then be used as an input to a second deep learning model or other machine learning model that is used to recognize an implantation quality, a preimplantation genetic screening result, a likelihood of viability, to predict the future development of a morphological feature, or determine another classification for the embryo (e.g., weight, gender, etc.) based on its morpho-kinetic signature. As the morpho-kinetic signature is itself a representation of the morpho-kinetic development of an embryo as a function of time, it provides a mechanism for assessing the development of the embryo as a whole. Thus, by generating a morpho-kinetic signature using a first deep learning model, the system may then input the morpho-kinetic signature into a second deep learning model to obtain an assessment of the embryo that provides a better prediction than any assessment based on a static image (and or individual morpho-kinetic events).

In some embodiments, the second deep learning model may comprise a plurality of separate deep learning models working in concert to generate the morpho-kinetic signature and/or a second deep learning model based on arrays with a varying number of vectors. For example, one of these deep learning models may be trained to classify cell splits (e.g., cell splits one through nine), the development of morula, the start of blastulation, and the pronuclei appearance and fading, whereas another deep learning model may be trained to classify an embryo into the one or more of the Gardner expansion degrees: (1) early blastocyst (e.g., where the blastocoel formed less than half of the volume of the embryo); (2) blastocyst (e.g., where the blastocoel formed more than half of the volume of the embryo); (3) full blastocyst (e.g., where the blastocoel completely filled the embryo); (4) expanded blastocyst (e.g., where the blastocoel volume was larger than that of the early embryo, and the zona had begun to thin); (5) hatching blastocyst (e.g., where the trophectoderm had begun to herniate though the zona); and (6) hatched blastocyst (e.g., where the blastocyst had completely escaped from the zona). Alternatively, a single deep learning model may comprise input arrays with vectors corresponding to one or more of the cell splits, the morula development, the start of blastulation, the pronuclei appearance and fading, and the Gardner expansion degrees.

In some embodiments, the deep learning models may additionally identify morphological features such as (a) fragmentation percent at two cells, (b) fragmentation percent at four cells (c) fragmentation percent at eight cells (d) blastomers symmetry at two cells, (e) blastomeres symmetry at four cells, (f) blastomers symmetry at eight cells, (g) an inner cell mass quality, (h) a trophectoderm quality, (g) cavity shape and area, (k) a zona pellucida thickness. These morphological features may comprise additional inputs (e.g., vectors) for a deep learning model or potential predictions of the deep learning model. For example, whereas traditional visual annotation methods may not be able to identify morphological features until they are visually present (e.g., over 5 days after fertilization), morpho-kinetic signature may be able to identify these features and/or predict when there will develop prior to them being visually present. Additionally or alternatively, the first deep learning model may identify the beginning and end (e.g., the point of clear separation) of each morpho-kinetic event. That is, the system may identify a plurality of stages for one or more morpho-kinetic events.

In some embodiments, the morpho-kinetic signature may be coupled with additional data. For example, the selection of the embryo may be based on a recommendation that is itself based on a combination of the analysis of the morpho-kinetic signature and preimplantation genetic tests. For example, the analysis of the morpho-kinetic signature may be coupled with PGD and/or PGS. Additionally or alternatively, in one embodiment, the morpho-kinetic signature may be coupled with other clinical data, such as age, weight, body mass index, endometrial thickness as well as other medical and demographic data (e.g., family history, race, etc.). For example, an input vector for an artificial neural network may have additional vectors representing the PGD, PGS, and/or clinical/demographic data.

The development of the morpho-kinetic signature as a mechanism for classifying embryos may also be used to expand available data sets for both training and testing purposes as the morpho-kinetic signature provides an additional data point for distinguishing between incomplete known implantation data (e.g., "KID unknown") or embryos scored on incomplete KID embryos (e.g., "KIDscored"). For example, at present KID embryos with complete data (e.g., "KID known") may be a source of training data for embryonic research. This data set may in some cases include a set of annotated images of an embryo's development. The embryos may correspond to embryos that were implanted (e.g., via IVF) into a uterus. However, in most cases, this data set is limited in that the ultimate viability of the embryo is not tracked. For example, two embryos, each having a high predicted viability, may have been implanted, but only one of the embryos was eventually viable. The inability to determine which of the embryos was eventually viable prevents this data from being used for training purposes. However, through a comparative analysis of morpho-kinetic signature generated (e.g., using the second deep learning model), the viable embryo may in many cases be determined. That is, if two embryos were implanted and one embryo eventually was viable the morpho-kinetic signatures for each may be compared. If one morpho-kinetic signature is high, whereas the other was low, the system can determine that the embryo corresponding to the high morpho-kinetic signature was the viable embryo. This prediction allows for KID embryos with undetermined viability to be used to expand the training and test data set.

Furthermore, a model may be trained based on training data that consists of both KID known and unknown embryos, using a modified target (=loss) function that is given to the learning process. This learning process is commonly referred to as "Semi-Supervised learning". In the later, the loss function of the training algorithm is modified (e.g., using a hinge-loss function) to output predictions that are generally required to match a group of outputs to a group of labels, rather than match a single label to a single output. Each group is defined by all the embryos that were jointly-transferred. The known embryos are a private case of this later definition with group of one (e.g., a group of KID unknown embryos that include only that embryo).

Additionally or alternatively, further expansion of data sets (both for training and testing) may be achieved through resampling existing data sets such as KID, and in particular estimating the distribution of a statistical estimator based on an imitation of the probabilistic structure of the data generating process and the morpho-kinetic signatures of a given set of randomly selected embryos in the current data set. For example, the system may further expand the data sets (both for training and testing) through bootstrapping of the data, where an initial model is trained by the system, and then evaluated on a "fresh" new, unlabeled dataset. Each embryo with "high enough" or "low enough" (e.g., with "enough" indicating a prediction score under/above a predetermined threshold) is assigned with a respective positive or negative label and added to the original training data set. The system may then use the new training set to train a new model, which is then used again to "bootstrap" more embryos from the fresh dataset. This process is repeated iteratively, until no further embryos are added.

In one aspect, the system may classify morphological and morpho-kinetic features in embryos. For example, the system may receive a first image of a first embryo. The system may label the first image with a known morphological or morpho-kinetic feature in the first image. The system may train an artificial neural network to detect the known morphological or morpho-kinetic feature in the first image. The system may receive a second image of a second embryo. The system may input the second image into the trained artificial neural network. The system may receive an output from the trained artificial neural network indicating that the second image includes the known morphological or morpho-kinetic feature.

In one aspect, the system may classify morpho-kinetic signatures in embryos. For example, the system may receive a first morpho-kinetic signature of a first embryo, wherein the first morpho-kinetic signature is a representation of morpho-kinetic events in the first embryo as a function of time. The system may label the first morpho-kinetic signature with a known classification. The system may train an artificial neural network to detect the known classification based on the first morpho-kinetic signature. The system may receive a second morpho-kinetic signature of a second embryo with an unknown classification, wherein the second morpho-kinetic signature is a representation of morpho-kinetic events in the second embryo as a function of time. The system may input the second morpho-kinetic signature into the trained artificial neural network. The system may receive a prediction from the trained artificial neural network that the second morpho-kinetic signature corresponds to the known classification.

In one aspect, the system may generate morpho-kinetic signatures for embryos. For example, the system may receive a first output from a first artificial neural network indicating that an embryo has a first classification at a first time point. The system may receive a second output from the first artificial neural network indicating the embryo has a second classification at a second time point. The system may aggregate the first output and second output to generate a morpho-kinetic signature, wherein the morpho-kinetic signature is a representation of morpho-kinetic events in the embryo as a function of time.

In one aspect, the system may predict viability of embryos based on morpho-kinetic signatures. For example, the system may receive a plurality of outputs from a first artificial neural network based on a series of images of an embryo. The system may generate a morpho-kinetic signature based on the plurality of outputs, wherein the morpho-kinetic signature is a representation of morpho-kinetic events in the embryo as a function of time. The system may input the morpho-kinetic signature into a second artificial neural network. The system may receive an output from the second artificial neural network indicating a viability of the embryo.

It should also be noted that one or more models discussed herein may be used jointly (and/or in parallel), where each model's prediction is considered a feature. For example, outputs (e.g., predictions) from a plurality of models may be received by the system and the system may determine which of the predictions to use and/or may combine the predictions. For example, each prediction may be a feature that may then be input into another model to select the best predictions based on an analysis of all of the predictions. For example, the final prediction may be the mean average of the each of the features. To combine these features, the system may use a machine learning algorithm such as Support Vector Machine ("SVM") or Random/Boosted trees to infuse all features (=all input models' predictions) into a single, robust model. Alternatively or additionally, one or more models discussed herein may be used in serial (e.g., results from one model (e.g., as described by FIG. 2) may be used for an input of another model (e.g., as described by FIG. 7).

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a part of, or the entirety of (i.e., the entire portion), a given item (e.g., data) unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

Figure 1:
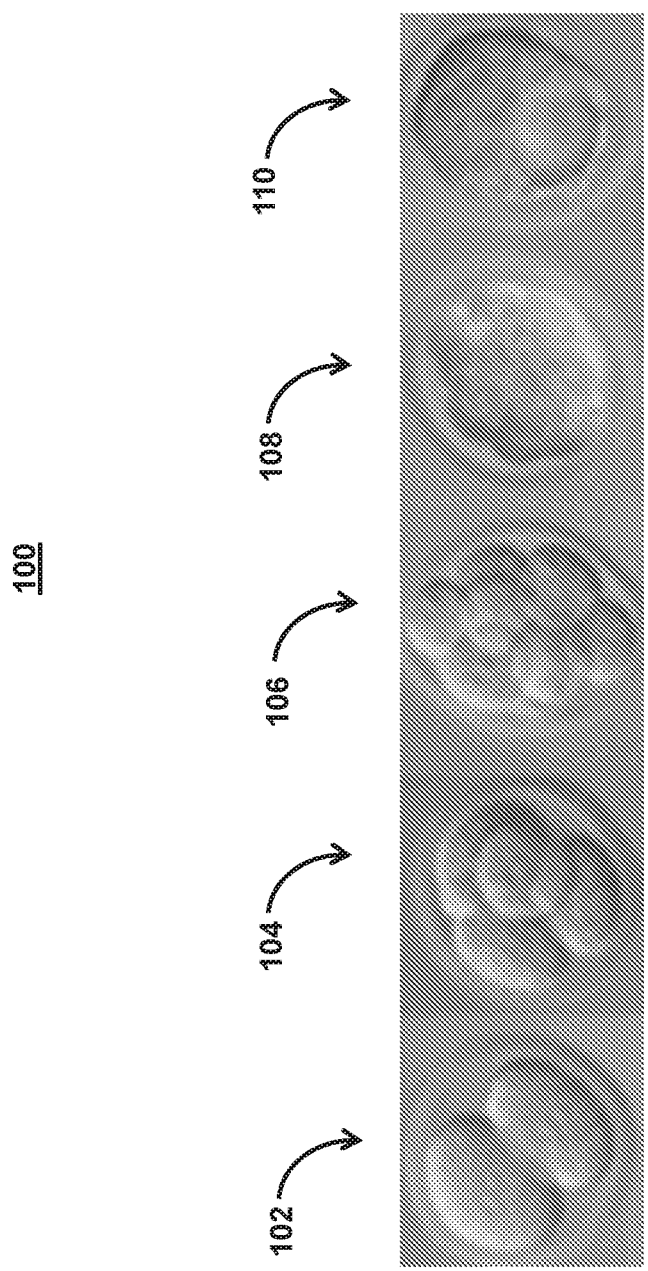
FIG. 1 shows a diagram of the morpho-logical changes undergone by an embryo during development, in accordance with one or more embodiments.

FIG. 1 shows a diagram of the morpho-logical changes undergone by an embryo during development, in accordance with one or more embodiments. For example, diagram 100 includes images of an embryo undergoing different morpho-kinetic events. As described herein, a morpho-kinetic event may include the appearance of a morphological feature and/or the achievement of a morphological stage. For example, a morphological feature may include any feature relating to a form, composition, or structure of an embryo and/or portion of an embryo. For example, a morphological feature may include one or more cell splits (e.g., cell splits one through nine), the development of morula, the start of blastulation, and the pronuclei appearance and fading. In another example, a morphological feature and/or achievement of a morphological stage may correspond to one or more of the Gardner expansion degrees: (1) early blastocyst (e.g., where the blastocoel formed less than half of the volume of the embryo); (2) blastocyst (e.g., where the blastocoel formed more than half of the volume of the embryo); (3) full blastocyst (e.g., where the blastocoel completely filled the embryo); (4) expanded blastocyst (e.g., where the blastocoel volume was larger than that of the early embryo, and the zona had begun to thin); (5) hatching blastocyst (e.g., where the trophectoderm had begun to herniate though the zona); and (6) hatched blastocyst (e.g., where the blastocyst had completely escaped from the zona).

In some embodiments, whether or not a morphological feature is present may depend on when the morphological feature is first distinguishable (e.g., a first appearance) or when the morphological feature is clearly separated from other features of a cell. In some embodiments, morphological features and/or achievements of a morphological stage may depend on whether or not a particular threshold is met. For example, the threshold may be keyed to a particular: (a) fragmentation percent at two cells; (b) fragmentation percent at four cells; (c) fragmentation percent at eight cells; (d) blastomers symmetry at two cells; (e) blastomers symmetry at four cells; (f) blastomers symmetry at eight cells; (g) inner cell mass; (h) trophectoderm; (g) cavity shape and area; or (k) zona pellucida thickness.

As shown in diagram 100, an embryo is transitioning through a series of morpho-kinetic events such as a two cell split (e.g., event 102), four cell split (e.g., event 104), eight cell split (e.g., event 106), morula development (e.g., event 108), blastocyst development (e.g., event 110). In some embodiments, each of the images in diagram 100 may be a single view and/or focal plane of the embryo at a given time point. For example, in some embodiments, the system may generate an image set of seven focal planes (e.g., to generate a three-dimensional view of the embryo). Furthermore, the seven images of diagram 100 may comprise only individual instances of a time-lapse video of the development of the embryo.

Figure 2:
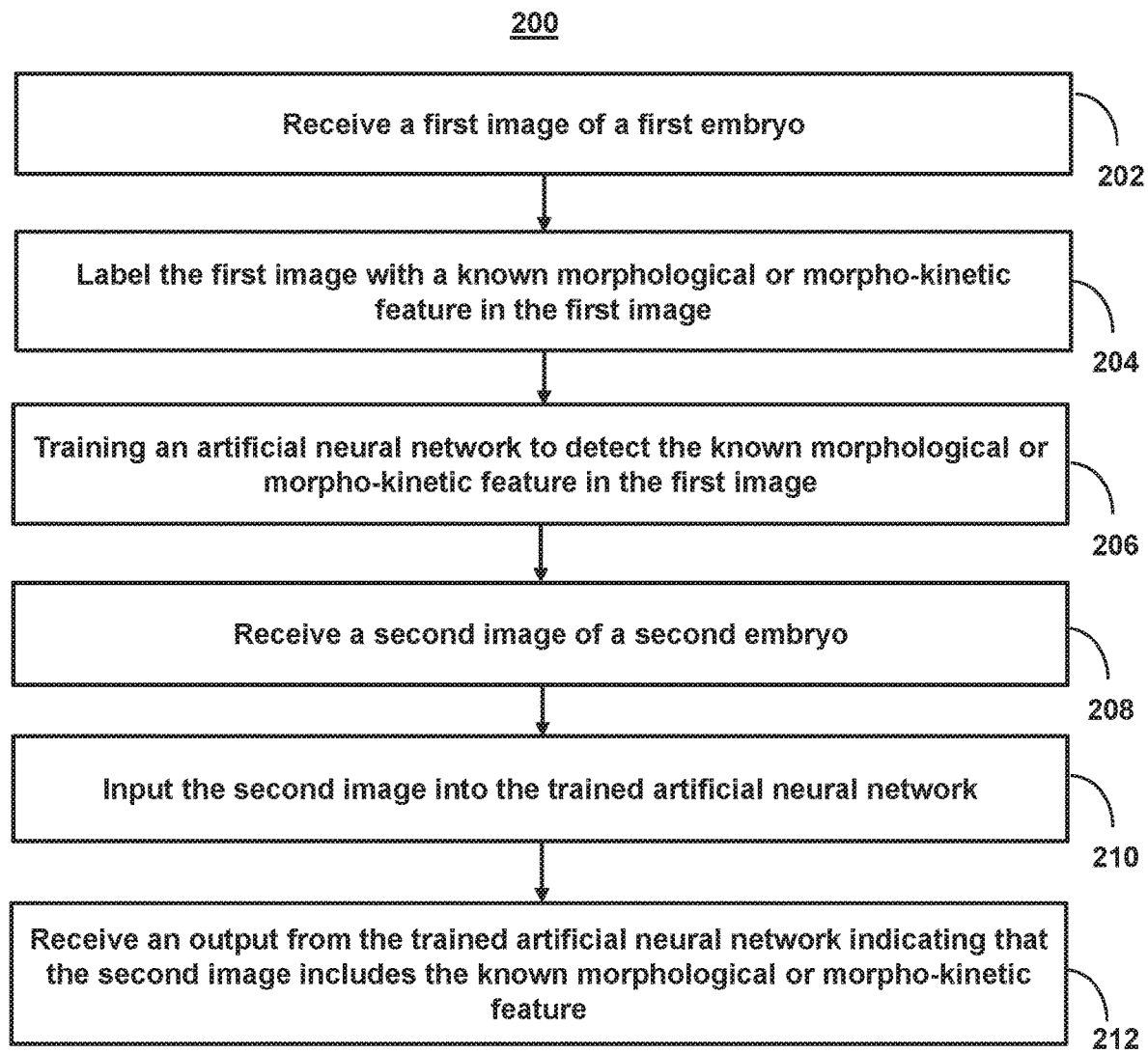
FIG. 2 shows a flowchart of the steps involved in classifying morphological and morpho-kinetic features, in accordance with one or more embodiments.

In some embodiments, the system may determine temporal distributions of morpho-kinetic events and time intervals between the consecutive events as determined both in manually annotated data and an artificial neural network (e.g., as described in FIG. 2). For example, using thousands of annotated profiles, the system may train a artificial neural network to successfully identify the morpho-kinetic event and time intervals between. For example, diagram 100 may represent one of 11,000 time-lapse video files of embryos cultured in one or more incubators. The embryos may be imaged using z-stacks, 10-20 μm apart, and may be recorded at ten to twenty minute intervals for one to six days. Morpho-kinetic events of all embryos may be annotated by embryologists in accordance with established protocols. The embryos may be divided into train, validation, and test sets. Test sets may consist of randomly selected subset of ten to twenty percent of all embryos. Test sets were strictly maintained uncontaminated and were used only after training processes were completed.

FIG. 2 shows a flowchart of the steps involved in classifying morphological and morpho-kinetic features, in accordance with one or more embodiments. Process 200 may be performed using the control circuitry of one or more components described in FIG. 3. For example, process 200 may relate to the use of an artificial neural network that has been trained on annotated data. For example, the annotated data may comprise static images at different development stages of an embryo (e.g., as shown in FIG. 1). The trained artificial neural network may then determine the development stage for each image in a series of images of an embryo. The trained artificial neural network may represent a first deep learning model, the outputs of which, are used to generate inputs for a second deep learning model, as discussed below in relation to FIG. 7.

At step 202, process 200 receives (e.g., using one or more components of system 300 (FIG. 3)) a first image of a first embryo. For example, in some embodiments, the first image may be based on an image set of a series of images of the embryo (e.g., time-lapse images). The image set may include multiple angles and/or views of the embryo. For example, the images of the embryo may include a Z stack featuring a plurality of frames (e.g., seven). The Z stack may comprise a compilation of images taken at a set interval between the first and last planes of focus.

In some embodiments, the system may generate a first pixel array based on the image of the embryo. For example, in some embodiments, the system may generate pixel arrays to represent the images. The pixel array may refer to computer data that describes the image (e.g., pixel by pixel). In some embodiments, this may include one or more vectors, arrays, and/or matrices that represent either a Red, Green, Blue colored or grayscale images. Furthermore, in some embodiments, the system may additionally convert the image from a set of one or more vectors, arrays, and/or matrices to another set of one or more vectors, arrays, and/or matrices. For example, the system may convert an image set having a red color array, a green color array, and a blue color to a grayscale color array. The array may have a varying number of vectors, and in some embodiments, the vectors may additional include data of clinical, demographic, or other data related to the embryo, which may be used to train the artificial neural network to identify a morphological and morpho-kinetic feature.

In some embodiments, the data set may include data based on known implantation data ("KID") embryos. KID embryos are not normally usable for training and testing artificial neural networks used for classifying morphological and morpho-kinetic features because KID embryos also depend on the capacity of the embryo to develop in the incubator under controlled conditions, implantation also depends on uterus receptivity, which is not taken into account in the training process. KID embryos are also preselected for transfer according to morphological and/or morpho-kinetic parameters (e.g., based on manual annotation of the data), which may introduce bias. It should be noted, as described below, through a comparative analysis of morpho-kinetic signature generated (e.g., using the second deep learning model), the viable embryo may in many cases be determined.

At step 204, process 200 labels (e.g., using one or more components of system 300 (FIG. 3)) the first image with a known morphological or morpho-kinetic feature in the first image. For example, the images may be generated about fifteen μm apart and at about twenty minute intervals during incubation of the embryos. This imaging may provide a continuous three-dimensional image of the embryo. The images may comprise a data set of thousands of embryos (e.g., greater than eleven thousand) and cultured in a plurality of incubators at remote locations. In some embodiments, each of these embryos is also tagged with additional clinical and/or other data (e.g., metadata) that is stored with the images. For example, the metadata may include maternal age, co-transferred embryo statistics, and implantation outcome.

At step 206, process 200 trains (e.g., using one or more components of system 300 (FIG. 3)) an artificial neural network to detect the known morphological or morpho-kinetic feature in the first image. For example, the system may train the artificial neural network, including the collection and preprocessing of data, as described in FIG. 4 below. The trained artificial neural network may classify the image of the embryo as corresponding to a morphological and/or a morpho-kinetic feature. For example, the trained artificial neural network may identify morphological features such as: (a) fragmentation percent at two cells; (b) fragmentation percent at four cells; (c) fragmentation percent at eight cells; (d) blastomers symmetry at two cells; (e) blastomers symmetry at four cells; (f) blastomers symmetry at eight cells; (g) inner cell mass; (h) trophectoderm; (g) cavity shape and area; or (k) zona pellucida thickness. Additionally or alternatively, the first trained artificial neural network may identify the beginning and end (e.g., the point of clear separation) of each morpho-kinetic event. That is, the system may identify a plurality of stages for one or more morpho-kinetic events.

For example, the trained artificial neural network may be trained to classify cell splits (e.g., cell splits one through nine), the development of morula, the start of blastulation, and the pronuclei appearance and fading and/or to classify an embryo into the one or more of the Gardner expansion degrees: (1) early blastocyst (e.g., where the blastocoel formed less than half of the volume of the embryo); (2) blastocyst (e.g., where the blastocoel formed more than half of the volume of the embryo); (3) full blastocyst (e.g., where the blastocoel completely filled the embryo); (4) expanded blastocyst (e.g., where the blastocoel volume was larger than that of the early embryo, and the zona had begun to thin); (5)

hatching blastocyst (e.g., where the trophectoderm had begun to herniate through the zona); and (6) hatched blastocyst (e.g., where the blastocyst had completely escaped from the zona). For example, the trained artificial neural network may comprise input arrays with vectors corresponding to one or more of the cells splits, the morula development, the start of blastulation, the pronuclei appearance and fading, and the Gardner expansion degrees.

At step 208, process 200 receives (e.g., using one or more components of system 300 (FIG. 3)) a second image of a second embryo. For example, the second image may be an image of an embryo for which has an unknown morphological or morpho-kinetic feature. For example, in some embodiments, the second image may be based on an image set of a series of images of the embryo (e.g., time-lapse images). The image set may include multiple angles and/or views of the embryo (e.g., a Z stack of images). In some embodiments, the system may generate a second pixel array based on the image of the embryo. For example, in some embodiments, the system may generate pixel arrays to represent the images. The pixel array may refer to computer data that describes the image (e.g., pixel by pixel). In some embodiments, the system may normalize the second array in order to account for bias in the system.

At step 210, process 200 inputs (e.g., using one or more components of system 300 (FIG. 3)) the second image into the trained artificial neural network. The system may process the input through one or more hidden layers (as described in FIG. 4 below) to classify the input as including a morphological or morpho-kinetic feature.

At step 212, process 200 receives (e.g., using one or more components of system 300 (FIG. 3)) an output from the trained artificial neural network indicating that the second image includes the known morphological or morpho-kinetic feature. For example, the trained artificial neural network may generate an output indicating that the image corresponds to a given class. As described below, this output may itself be used to generate an input (e.g., a second vector array) that in input into a second deep learning model (e.g., a second artificial neural network).

Figure 5:
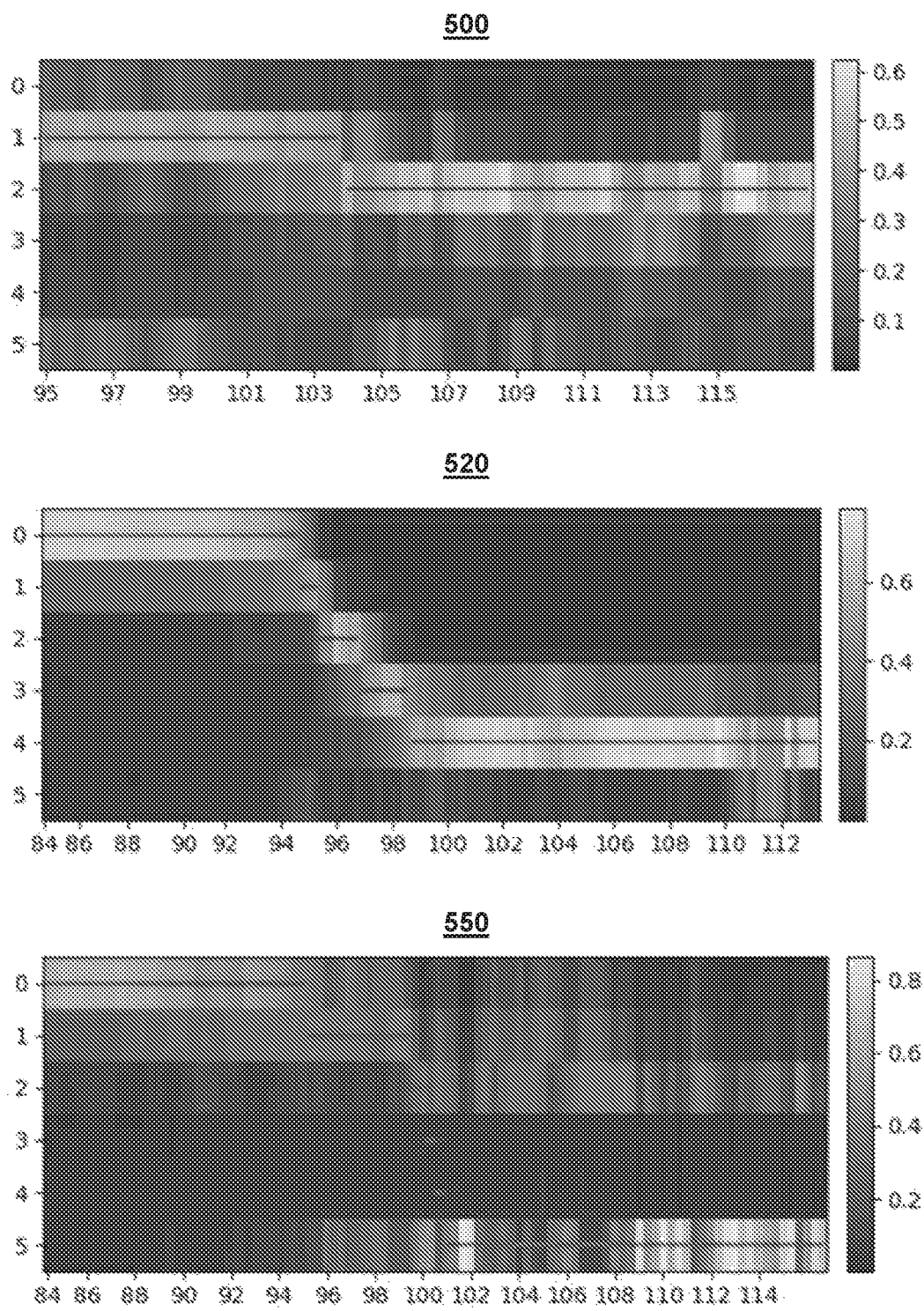
FIG. 5 shows an exemplary visual representation of a morpho-kinetic signatures based on a first set of vectors, in accordance with one or more embodiments.
Figure 6:
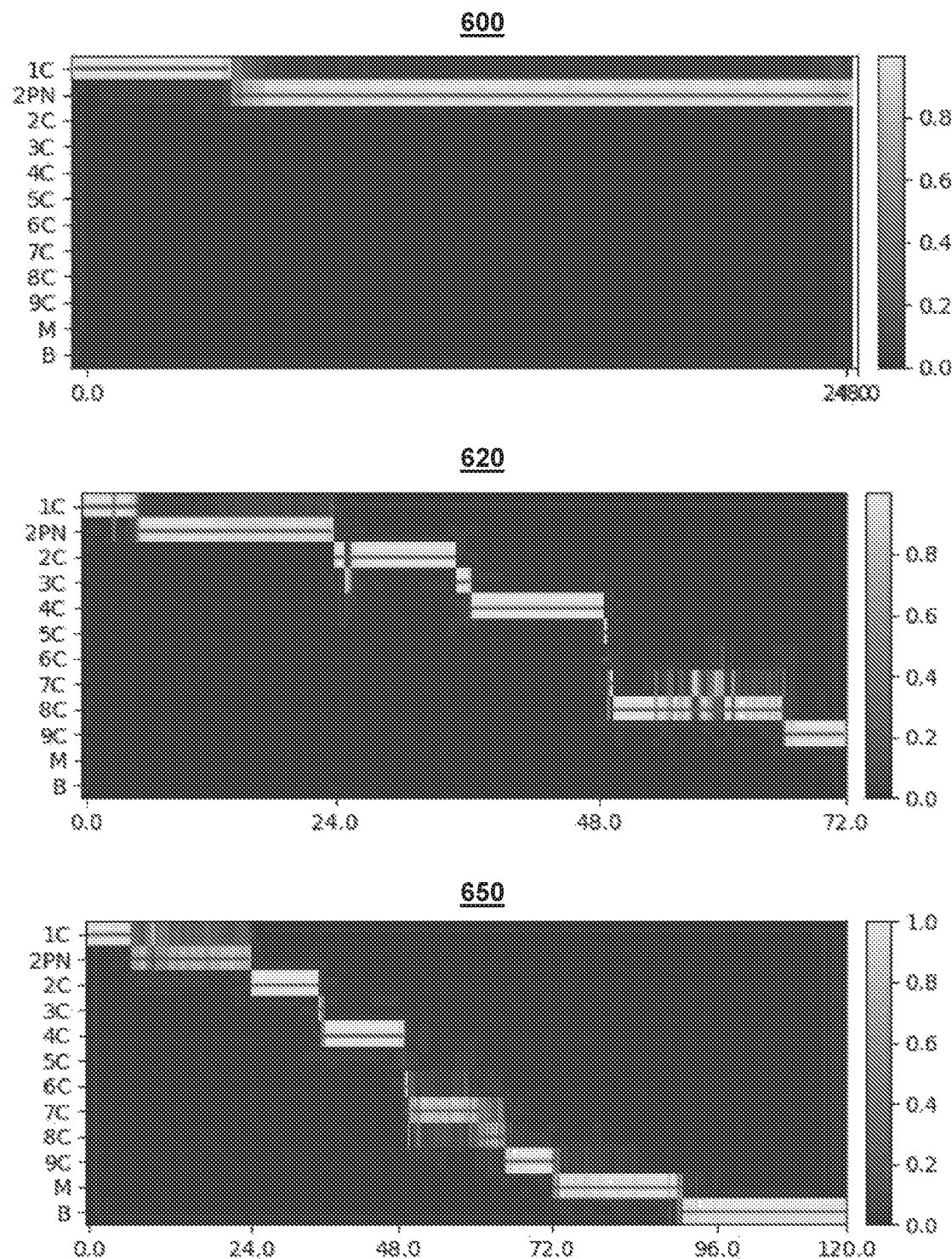
FIG. 6 shows an exemplary visual representation of a morpho-kinetic signatures based on a second set of vectors, in accordance with one or more embodiments.

Furthermore, the system may receive a series of images (e.g., a time-lapse of images) of the second embryo. The trained artificial neural network may output a determined morphological or morpho-kinetic feature for each image in the series of images for the embryo. In some embodiments, the output may comprise a float-point number (e.g., between one and zero) corresponding to a probability that the embryo corresponds to a classification of a morphological or morpho-kinetic feature. The system may then compile the series of outputs (e.g., the series of vector arrays each corresponding to a different time point) to generate a representation of the development of the embryo as a function of time. In some embodiments, the series of outputs may be converted into a visual representation (e.g., a heat map) as shown in FIGS. 5-6 below.

Figure 3:
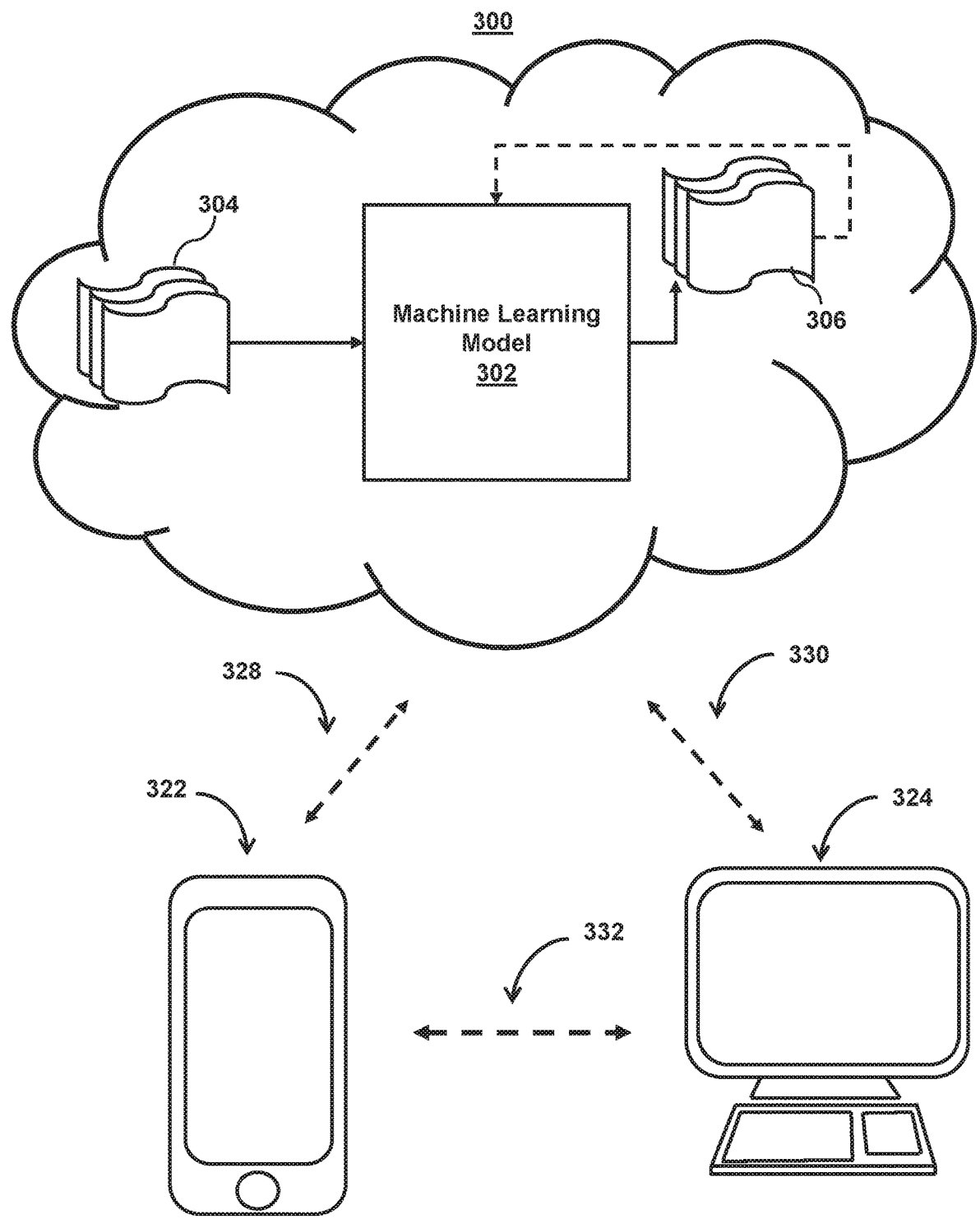
FIG. 3 shows an illustrative system upon which to implement methods and systems for embryo classification using morpho-kinetic signatures, in accordance with one or more embodiments.

FIG. 3 shows an illustrative system upon which to implement methods and systems for embryo classification using morpho-kinetic signatures, in accordance with one or more embodiments. As shown in FIG. 3, system 300 may include user device 322, user device 324, and/or other components. Each user device may include any type of mobile terminal, fixed terminal, or other device. Each of these devices may receive content and data via input/output (hereinafter "I/O") paths and may also include processors and/or control circuitry to send and receive commands, requests, and other suitable data using the I/O paths. The control circuitry may be comprised of any suitable processing circuitry. Each of these devices may also include a user input interface and/or display for use in receiving and displaying data.

By way of example, user device 322 and user device 324 may include a desktop computer, a server, or other client device. Users may, for instance, utilize one or more of the user devices to interact with one another, one or more servers, or other components of system 300. It should be noted that, while one or more operations are described herein as being performed by particular components of system 300, those operations may, in some embodiments, be performed by other components of system 300. As an example, while one or more operations are described herein as being performed by components of user device 322, those operations may, in some embodiments, be performed by components of user device 324. System 300 also includes machine learning model 302, which may be implemented on user device 322 and user device 324, or accessible by communication paths 328 and 330, respectively. It should be noted that, although some embodiments are described herein with respect to machine learning models, other prediction models (e.g., statistical models or other analytics models) may be used in lieu of, or in addition to, machine learning models in other embodiments (e.g., a statistical model replacing a machine learning model and a non-statistical model replacing a non-machine learning model in one or more embodiments).

Each of these devices may also include memory in the form of electronic storage. The electronic storage may include non-transitory storage media that electronically stores information. The electronic storage of media may include: (i) system storage that is provided integrally (e.g., substantially non-removable) with servers or client devices; and/or (ii) removable storage that is removably connectable to the servers or client devices via, for example, a port (e.g., a USB port, a firewire port, etc.) or a drive (e.g., a disk drive, etc.). The electronic storages may include optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

FIG. 3 also includes communication paths 328, 330, and 332. Communication paths 328, 330, and 332 may include the Internet, a mobile phone network, a mobile voice or data network (e.g., a 4G or LTE network), a cable network, a public switched telephone network, or other types of communications network or combinations of communications networks. Communication paths 328, 330, and 332 may include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

As an example, with respect to FIG. 3, machine learning model 302 may take inputs 304 and provide outputs 306. The inputs may include multiple data sets such as a training data set and a test data set. In some embodiments, outputs 306 may be fed back to machine learning model 302 as input to train machine learning model 302 (e.g., alone or in conjunction with user indications of the accuracy of outputs 306, labels associated with the inputs, or with other reference feedback information). In another embodiment, machine learning model 302 may update its configurations (e.g., weights, biases, or other parameters) based on the assessment of its prediction (e.g., outputs 306) and reference feedback information (e.g., user indication of accuracy, reference labels, or other information). In another embodiment, where machine learning model 302 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 302 may be trained to generate better predictions.

In some embodiments, machine learning model 302 may include an artificial neural network. In such embodiments, machine learning model 302 may include input layer and one or more hidden layers. Each neural unit of machine learning model 302 may be connected with many other neural units of machine learning model 302. Such connections can be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Machine learning model 302 may be self-learning and trained, rather than explicitly programmed, and can perform significantly better in certain areas of problem solving, as compared to traditional computer programs. During training, an output layer of machine learning model 302 may correspond to a classification of machine learning model 302 and an input known to correspond to that classification may be input into an input layer of machine learning model 302 during training. During testing, an input without a known classification may be input into the input layer, and a determined classification may be output.

In some embodiments, machine learning model 302 may include multiple layers (e.g., where a signal path traverses from front layers to back layers). In some embodiments, back propagation techniques may be utilized by machine learning model 302 where forward stimulation is used to reset weights on the "front" neural units. In some embodiments, stimulation and inhibition for machine learning model 302 may be more free-flowing, with connections interacting in a more chaotic and complex fashion. During testing, an output layer of machine learning model 302 may indicate whether or not a given input corresponds to a classification of machine learning model 302). Machine learning model 302 may be used to classify morphological and morpho-kinetic features. For example, the machine learning model 302 may input an image (or images) of an embryo and receive an output classify the embryo as corresponding to morphological and morpho-kinetic features.

In some embodiments, system 300 may use simulated labels and/or bootstrap labels to refine and/or improve one or more models described herein. For example, system 300 may simulate labels for known implantation data that is partial or incomplete. In the case of simulated labels, system 300 may receive embryo data (e.g., known implantation data) that include images of the embryos' development (e.g., time-lapse images), but does not include labeled classifications corresponding to the embryos' development (e.g., an implantation quality, a preimplantation genetic screening result, a likelihood of viability, a prediction of the future development of a morphological feature, or another classification for the embryo (e.g., weight, gender, etc.).

The system may generate the labeled classification based on a review of the morph-kinetic signatures of the embryos (e.g., as generate by system 300 using the images of an embryo's development) as well as information about the viability of additional embryos implanted with the embryo. For example, if the embryo was implanted with one other embryo, and only one embryo resulted in a viable embryo, the system may compare the morph-kinetic signatures of the embryos. If one of the morph-kinetic signatures has a high predicted score (e.g., indicating a high probability of viability) and the other morph-kinetic signature has a low predicted score (e.g., indicating a low probability of viability of the embryos. The system may generate a simulated label that the embryo with the morph-kinetic signature that has a high predicted score as viable and/or that the embryo with the morph-kinetic signature that has a low predicted score as not viable. This information may be used to grow a data set of information that may be used to train, and further improve, an artificial neural network (e.g., as described in FIGS. 7-9).

Additionally or alternative, system 300 may generate additional training data through the use of bootstrap aggregation. For example, system 300 may access embryo data (e.g., known implantation data) that has no labels. System 300 may then apply a bootstrapping model to the unlabeled data to identify embryos with a predicted classification that is above a threshold confidence. For example, system 300 may receive data for one-thousand embryos. System 300 may generate morpho-kinetic signatures for the embryos, but have not information on one or more classifications (e.g., in contrast to the simulated labels above). System 300 may however apply a model to the morpho-kinetic signatures for the embryos that determine, with a predetermined level of confidence, the morpho-kinetic signatures for the embryos that resulted in a given classification (e.g., a viable embryo) based on the currently available training data. If one-hundred embryos meet the threshold, the on-hundred embryos may be added to the training data.

For example, system 300 may generate a prediction score (e.g., corresponding to a float point value) indicating a probability of a given morpho-kinetic signature corresponding to a given classification. System 300 may then compare the prediction scores to the prediction scores of existing training data. System 300 may determine a threshold score above which any prediction score corresponds to a given classification (e.g., a viable embryo). In response to identifying morpho-kinetic signatures with a prediction score above this threshold, system 300 may designate these morpho-kinetic signatures as corresponding to the classification. System 300 may then add these morpho-kinetic signatures with their labeled classification to the training set of data.

System 300 may iteratively adjust the model based on additional data to continually lower the threshold score above which any prediction score corresponds to the given classification. For example, as system 300 receives more training data, system 300 may refine the artificial neural network and/or other machine learning algorithm to better predict whether or not a given morpho-kinetic signature corresponds to a given classification.

Figure 4:
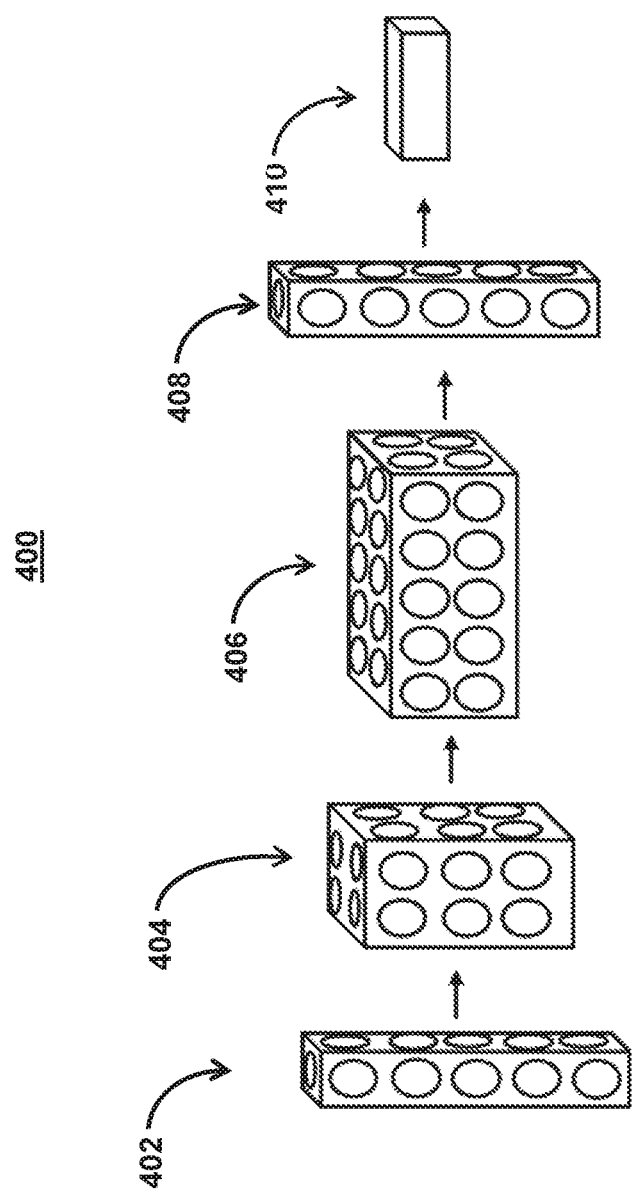
FIG. 4 shows a neural network used for classifying embryos, in accordance with one or more embodiments.

FIG. 4 shows a graphical representations of artificial neural network models for classifying embryos, in accordance with one or more embodiments. Model 400 illustrates an artificial neural network. Model 400 includes input layer 402. Images (or vector arrays based on images) may be entered into model 400 at this level. Model 400 also includes one or more hidden layers (e.g., hidden layers 404, 406, and 408). Model 400 may be based on a large collection of neural units (or artificial neurons). Model 400 loosely mimics the manner in which a biological brain works (e.g., via large clusters of biological neurons connected by axons). Each neural unit of a model 400 may be connected with many other neural units of model 400. Such connections can be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Model 400 may be self-learning and trained, rather than explicitly programmed, and can perform significantly better in certain areas of problem solving, as compared to traditional computer programs. During training, output layer 410 may correspond to a classification of model 400 (e.g., whether or not a given image set corresponds to a genotype biomarker) and an input known to correspond to that classification may be input into input layer 402. In some embodiments, model 400 may include multiple layers (e.g., where a signal path traverses from front layers to back layers). In some embodiments, back propagation techniques may be utilized by model 400 where forward stimulation is used to reset weights on the "front" neural units. In some embodiments, stimulation and inhibition for model 400 may be more free-flowing, with connections interacting in a more chaotic and complex fashion. Model 400 also includes output layer 410. During testing, output layer 410 may indicate whether or not a given input corresponds to a classification of model 400 (e.g., whether or not an image corresponds to a morphological and/or morpho-kinetic feature and/or a morpho-kinetic signature corresponds to a viable embryo).

In some embodiments, embryo video files may undergo preprocessing. For example, the system may reduce the size of images by identifying and discarding empty well images, cropping the images to portions that contain the embryos, and down-sampling the cropped images. In some embodiments, the system may also automatically determine whether or not a well includes an embryo. For example, the system may determine in each pixel, the 2-norm of the absolute values of both channels is calculated to generate a gradient map which is then normalized by the median gradient value.

Model 400 may be a convolutional neural network ("CNN"). The convolutional neural network is an artificial neural network that features one or more convolutional layers. Convolution layers extract features from an input image. Convolution preserves the relationship between pixels by learning image features using small squares of input data. For example, the relationship between the individual parts of the image of the embryo and/or morpho-kinetic signature may be preserved.

The input of the CNN are preprocessed packets of embryo and time index. The time index correlates the image as a function of time. The CNN architecture consists of multiple hidden layers (e.g., layer 404 through 408). The last layer (e.g., layer 408) may have six input neurons. The output neuron (e.g., output layer 410), which is the packet score, is selected according to the time index of the packet. The packet score creates a numerical representation of the image.

FIG. 5 shows an exemplary visual representation of a morpho-kinetic signatures based on a first set of vectors, in accordance with one or more embodiments. For example, as shown in image 500, image 520, and image 550 is a visual representation (e.g., a heat map) of a morpho-kinetic signature. The x-axis of each image corresponds to time, whereas the y-axis corresponds to a particular morpho-kinetic event (e.g., Gardner expansion degrees). The color variations of each image, as described by the legend, indicates a float value for each morpho-kinetic event (e.g., a float value between zero and one). The float value may be used as an indicator of the probability and/or appearance of indicia of the morpho-kinetic event. Image 500 corresponds to an embryo achieving early blastocyst. Image 520 corresponds to an embryo hatching blastocyst, and image 550 corresponds to an embryo reaching hatched blastocyst.

FIG. 6 shows another exemplary visual representation of a morpho-kinetic signatures based on a second set of vectors, in accordance with one or more embodiments. For example, as shown in image 600, image 620, and image 650 is a visual representation (e.g., a heat map) of a morpho-kinetic signature. In contrast to FIG. 5, the x-axis corresponds morpho-kinetic events such as cell splits, pronuclei appearance, development of morula, and the start of blastulation. For example, image 600 corresponds to an embryo reaching pronuclei appearance. Image 620 corresponds to a ninth cell split, and image 650 corresponds to the start of blastulation.

As shown by FIGS. 5-6, the morpho-kinetic signature of the development of each embryo acts as a fingerprint from which the system may determine one or more classifications. Based on the morpho-kinetic events, including the appearance, rate, and/or combination with additional data (e.g., clinical data, preimplantation genetic screening, etc.), the system may classify a given embryo. In some embodiments, the system may additionally use the morpho-kinetic signatures to predict, when, if, the size of, and/or other characteristics of morpho-kinetic events. For example, using a morpho-kinetic signature of an embryo's pronuclei appearance, the system may determine when the embryo will achieve the ninth cell split. It should also be noted that while FIGS. 5-6 represent visual representations of underlying numerical morpho-kinetic signatures, in some embodiments, the visual representations themselves may act as input to an artificial neural network as described herein.

It should also be noted that FIGS. 5-6 are illustrative only and not meant to be limiting. For example, in some embodiments, the system may use morpho-kinetic signatures with a varying number of vectors. For example, in one embodiment, a morpho-kinetic signature may have eleven vectors corresponding to eleven morphological stages (e.g., each vector corresponding to stage). Alternatively, in one embodiment, a morpho-kinetic signature may have twenty vectors corresponding to thirteen cell splits and 6 stages of blastocyst.

Figure 7:
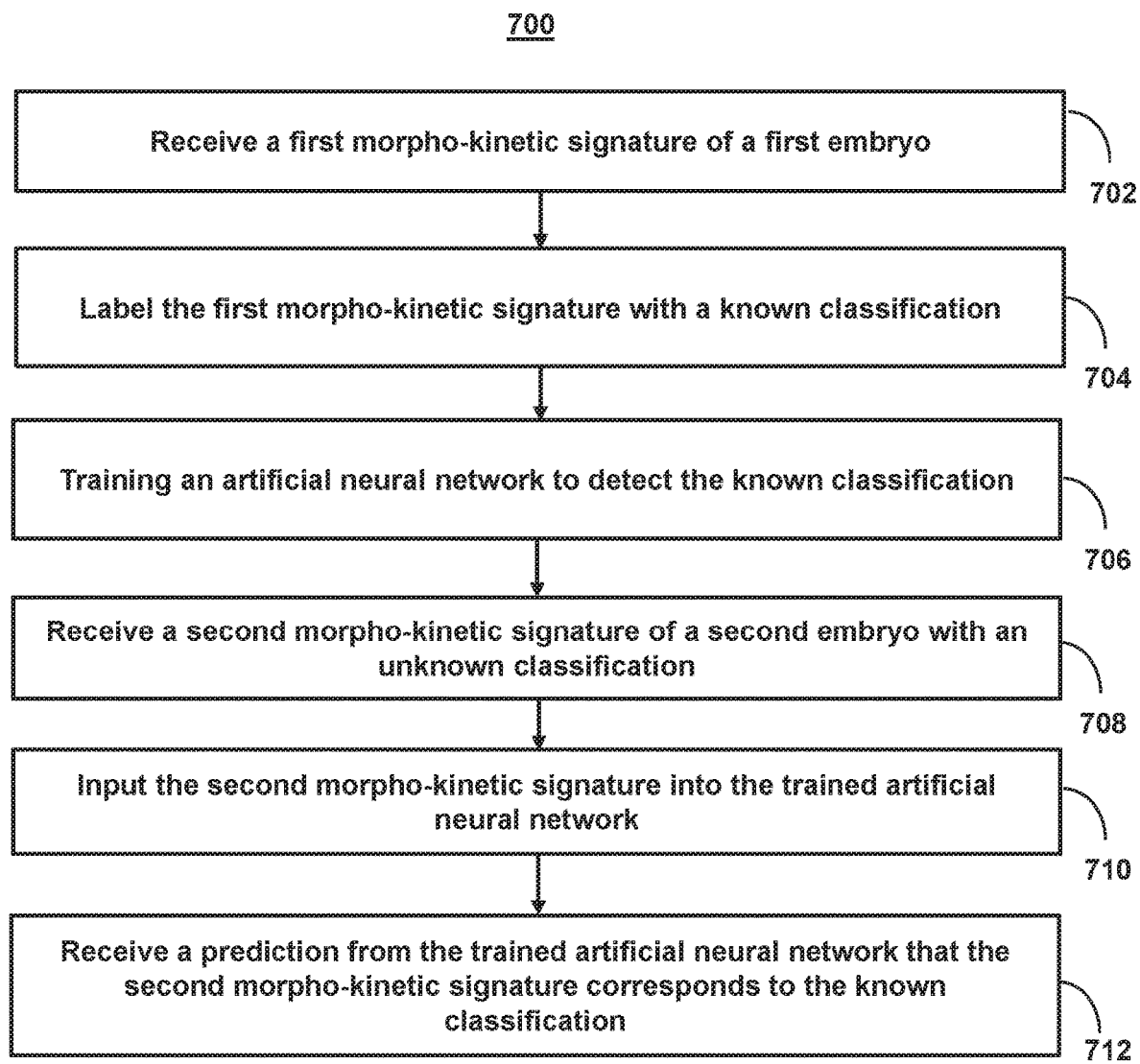
FIG. 7 shows a flowchart of the steps involved in embryo classification using morpho-kinetic signatures, in accordance with one or more embodiments.

FIG. 7 shows a flowchart of the steps involved in embryo classification using morpho-kinetic signatures, in accordance with one or more embodiments. For example, process 700 may describe the use of the morpho-kinetic signatures as represented in FIGS. 5-6 as generated by a artificial neural network as described in FIGS. 3-4.

At step 702, process 700 (e.g., via one or more components of system 300 (FIG. 3)) receives a first morpho-kinetic signature of a first embryo. For example, the first morpho-kinetic signature may be a representation of morpho-kinetic events in the first embryo as a function of time. In one example, the first morpho-kinetic signature may be based on a series of time-lapse images of the morpho-kinetic events in the first embryo (e.g., as captured while the first embryo is being incubated).

In some embodiments, the morpho-kinetic signature may be a vector array that numerically describes the morpho-kinetic events in the first embryo. For example, each of the morpho-kinetic events may be represented as a float value (e.g., from zero to one) in a vector. A value of zero may indicate that the morpho-kinetic event corresponding to the vector is non-present, whereas a value of one may indicate that the morpho-kinetic event is present. The float value may be used to apply a percentage or probability of the morph-kinetic event occurring.

In some embodiments, a morpho-kinetic event may be an appearance of a morphological features in the first embryo and/or a rate of development for the morphological feature. For example, the morpho-kinetic event may correspond to a cell split (e.g., cell splits one through nine), a development of a morula, a start of blastulation, a pronuclei appearance, or a pronuclei fading. Moreover, the morpho-kinetic event may include a first appearance of a morphological feature among other morphological features and/or a clear separation of the morphological feature from the other morphological features.

Additionally or alternatively, the morpho-kinetic event may be an achievement of a Garner expansion degree such as: (1) early blastocyst (e.g., where the blastocoel formed less than half of the volume of the embryo); (2) blastocyst (e.g., where the blastocoel formed more than half of the volume of the embryo); (3) full blastocyst (e.g., where the blastocoel completely filled the embryo); (4) expanded blastocyst (e.g., where the blastocoel volume was larger than that of the early embryo, and the zona had begun to thin); (5) hatching blastocyst (e.g., where the trophectoderm had begun to herniate though the zona); and (6) hatched blastocyst (e.g., where the blastocyst had completely escaped from the zona).

Additionally or alternatively, the morpho-kinetic event may correspond to a fragmentation percent at two cells, a fragmentation percent at four cells, a fragmentation percent at eight cells, blastomers symmetry at two cells, blastomers symmetry at four cells, blastomers symmetry at eight cells, inner cell mass quality, trophectoderm quality, cavity shape, cavity area, cavity percentage, and/or zona pellucida thickness.

At step 704, process 700 (e.g., via one or more components of system 300 (FIG. 3)) labels the first morpho-kinetic signature with a known classification. For example, the known classification may correspond to an implantation quality, a likelihood of viability, a preimplantation genetic screening result, or a predicted morphological feature.

At step 706, process 700 (e.g., via one or more components of system 300 (FIG. 3)) trains an artificial neural network to detect the known classification based on the first morpho-kinetic signature. For example, the system may use one or more artificial neural networks as described above in FIGS. 3-4.

At step 708, process 700 (e.g., via one or more components of system 300 (FIG. 3)) receives a second morpho-kinetic signature of a second embryo with an unknown classification. For example, the second morpho-kinetic signature may be a representation of morpho-kinetic events in the second embryo as a function of time. In some embodiments, the system may also receive additional information with the second morpho-kinetic signature. Additional information may include preimplantation genetic diagnosis or preimplantation genetic screening data. Additional information may also include clinical data such as age, weight, body mass index, endometrial thickness as well as other medical and demographic data (e.g., family history, race, etc.).

At step 710, process 700 (e.g., via one or more components of system 300 (FIG. 3)) inputs the second morpho-kinetic signature into the trained artificial neural network. In some embodiments, in which the system also uses additional information, the system may label the first morpho-kinetic signature with first additional information about the first embryo, train the artificial neural network to detect the known classification based on the first morpho-kinetic signature and the first additional information, receive second additional information about the second embryo, and input the second additional information along with the second morpho-kinetic signature into the trained artificial neural network to receive the prediction.

At step 712, process 700 (e.g., via one or more components of system 300 (FIG. 3)) receives a prediction from the trained artificial neural network that the second morpho-kinetic signature corresponds to the known classification. For example, the system may provide a prediction that indicates that the embryo corresponding to the second morpho-kinetic signature corresponds to the known classification. For example, the classification may indicate that the embryo has a high implantation quality, a high likelihood of viability, a specific preimplantation genetic screening result, or a predicted morphological feature (or date when a morphological feature will appear). For example, the morpho-kinetic signature may be used to predict when a morphological feature will appear.

For example, the prediction may comprise a prediction score (e.g., a float value between one and zero), which indicates a likelihood of the embryo corresponding to the known classification (e.g., the viability of the embryo if implanted), where a one score indicates a strong correlations (e.g., corresponds to high viability) and a zero score indicates a low correlations (e.g., corresponds to a low viability). Alternatively, the prediction may include a binary determination of whether or not the embryo corresponds to a given classification.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1 and 3-4 could be used to perform one or more of the steps in FIG. 7.

Figure 8:
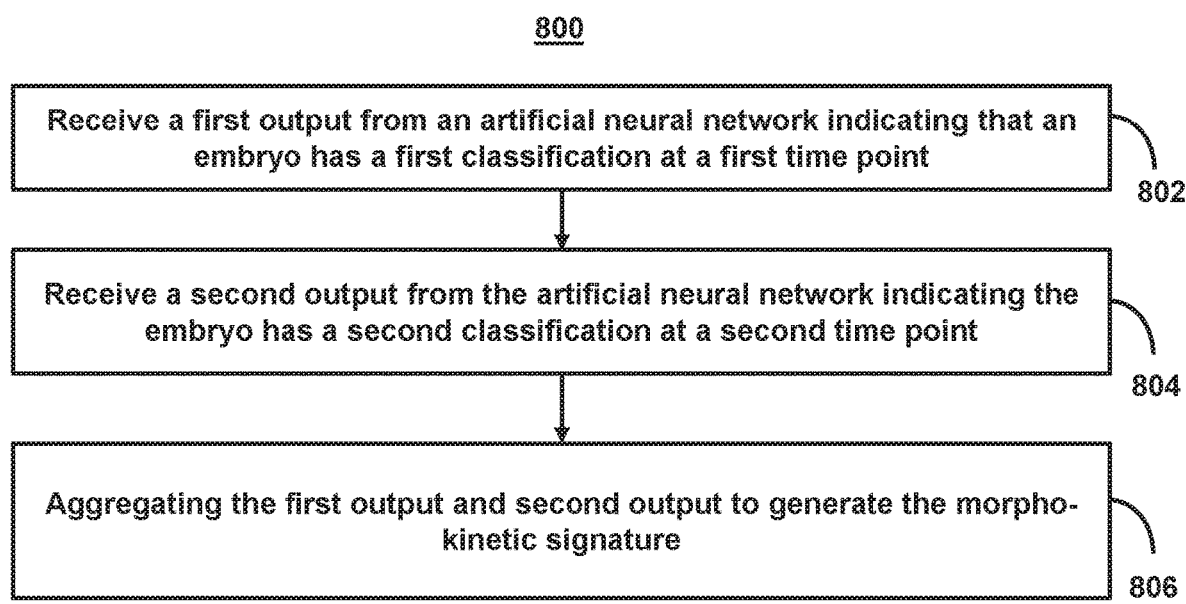
FIG. 8 shows a flowchart of the steps involved in generating morpho-kinetic signatures for embryos, in accordance with one or more embodiments.

FIG. 8 shows a flowchart of the steps involved in generating morpho-kinetic signatures for embryos, in accordance with one or more embodiments. For example, process 800 may described an embodiment for generating the morpho-kinetic signatures used in FIGS. 7 and 9.

At step 802, process 800 (e.g., via one or more components of system 300 (FIG. 3)) receives a first output from an artificial neural network indicating that an embryo has a first classification at a first time point. For example, the artificial neural network may correspond to the artificial neural network described in FIG. 2 above.

For example, the system may receive an annotated image of a training data embryo. For example, the training data embryo may be annotated with a known morphological or morpho-kinetic feature. The system may then train the initial artificial neural network to classify images with the known morphological or morpho-kinetic feature in the first classification. Once trained, the system may receive a first image of the first embryo that is input into the initial artificial neural network. The system may then receive the first output from the initial artificial neural network indicating that the first image includes the known morphological or morpho-kinetic feature.

At step 804, process 800 (e.g., via one or more components of system 300 (FIG. 3)) receives a second output from the first artificial neural network indicating the embryo has a second classification at a second time point. In some embodiments, the system may use known implantation data in order to increase the amount of training data available. One drawback of known implantation data is that the known implantation data may be incomplete. That is, known implantation data may not indicate whether or not an embryo was viable. Additionally or alternatively, the known implantation data may have lapses in the images of the embryo during incubation, resulting in an incomplete morpho-kinetic signature.

In some embodiments, the system may preprocess incomplete data (e.g., known implantation data) through bootstrapping or other processes. For example, the system may use bootstrapping, a statistical tool, to generate an additional sample set of training data. For example, data on embryo viability and/or time-lapse images of incubating embryos may not be available. In such cases, the system may resample data from the existing data set. For example, the system may resample test data (e.g., which was previous separated from training data) to generate more training data. The system may resample the data to ensure that the resampled data is randomly and independently generated from the test data.

For example, the system may receive known implantation data indicating that the first embryo has a first classification at a first time point. The system may then generate a bootstrap label based on the known implantation data, wherein the bootstrap label corresponds to a second classification at a second time point. The system may then aggregate the first classification and the second classification to generate the first morpho-kinetic signature.

At step 806, process 800 (e.g., via one or more components of system 300 (FIG. 3)) aggregates the first output and second output to generate a morpho-kinetic signature. For example, the morpho-kinetic signature is a representation of morpho-kinetic events in the embryo as a function of time. For example, each output may correspond to a single time-lapse image. The system may determine the morpho-kinetic event in each time-lapse image and generate a vector value corresponding to the morpho-kinetic event. The system may then aggregate these values to generate the morpho-kinetic signature.

It is contemplated that the steps or descriptions of FIG. 8 may be used with any other embodiment of this disclosure. In addition, the steps and descriptions described in relation to FIG. 8 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1 and 3-4 could be used to perform one or more of the steps in FIG. 8.

Figure 9:
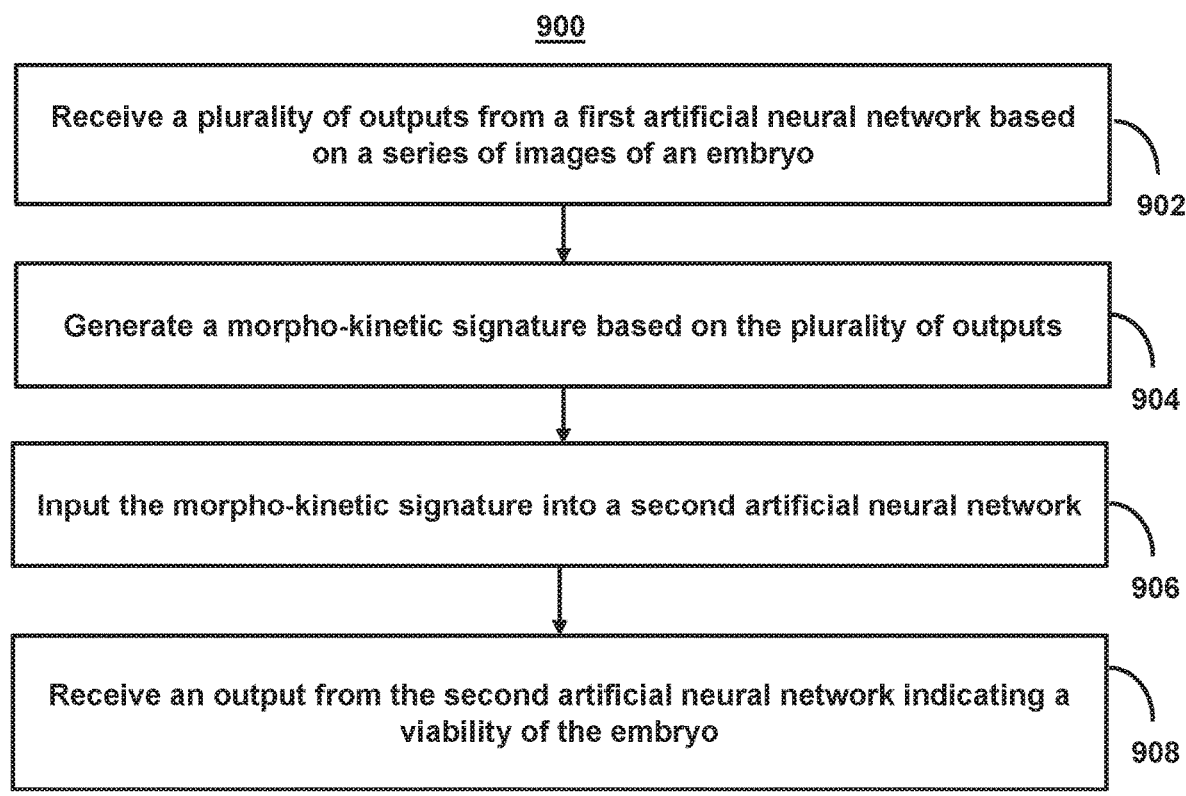
FIG. 9 shows a flowchart of the steps involved in using morpho-kinetic signatures to predict viability of embryos, in accordance with one or more embodiments.

FIG. 9 shows a flowchart of the steps involved in using morpho-kinetic signatures to predict viability of embryos, in accordance with one or more embodiments. It should be noted that in addition to predicting the viability of embryos, the steps of process 900 may be used for other classifications (e.g., an implantation quality, a preimplantation genetic screening result, a likelihood of viability, or a predicted morphological feature).

At step 902, process 900 (e.g., via one or more components of system 300 (FIG. 3)) receives a plurality of outputs from a first artificial neural network based on a series of images of an embryo. For example, the system may determine a series of morpho-kinetic events that correspond to a series of time-lapse images of an embryo during incubation. The system may use an initial artificial neural network (e.g., as described in FIG. 2) to perform this function.

At step 904, process 900 (e.g., via one or more components of system 300 (FIG. 3)) generates a morpho-kinetic signature based on the plurality of outputs. For example, the morpho-kinetic signature may be a representation of morpho-kinetic events in the embryo as a function of time. In some embodiments, the system may further generate graphical representations of the morpho-kinetic signature as shown in FIGS. 5-6.

At step 906, process 900 (e.g., via one or more components of system 300 (FIG. 3)) inputs the morpho-kinetic signature into a second artificial neural network. For example, the system may have trained the second artificial neural network to classify inputted morpho-kinetic signatures. In some embodiments, the system may train the second artificial neural network on labeled morph-kinetic signatures (e.g., morpho-kinetic signatures annotated as corresponding to a high or low viability embryo).

In some embodiments, the system may generate the first morpho-kinetic signature of the first embryo based on known implantation data and may determine a classification for the first morpho-kinetic signature through a comparison of other morpho-kinetic signatures. For example, in order to increase the amount of training data for the system, the system may use known implantation data. Known implantation may include time-lapse images of embryos (e.g., for use in generating a morpho-kinetic signature). However, the known implantation data may lack a label as to whether or not the embryo was viable. This may be particularly true as the viability of the embryo may depend on additional factors after implantation (e.g., the conditions of the uterus, etc.). Moreover, the ultimate viability may not be determinable if multiple embryos were implanted, but only a single embryo become viable.

To determine which of the embryos became viable, the system may compare the morpho-kinetic signatures. These morpho-kinetic signatures comprise an additional data point with which to use to determine which of the embryos became viable. For example, the system may match each of the morpho-kinetic signatures to morpho-kinetic signatures that are already labeled as viable. If one implanted embryo has a morpho-kinetic signature with a high correlation to the morpho-kinetic signatures of viable embryos and one implanted embryo does not have a high correlation to the morpho-kinetic signatures of viable embryos, the system can determine that the embryo with the high correlation was the viable embryo. This embryo (and its morpho-kinetic signature) may then be added to the data set as a morpho-kinetic signature resulting in a viable embryo. Likewise, the converse is true for the other embryo and its morpho-kinetic signature.

For example, the system may determine the known classification for the first embryo (e.g., an implantation quality, a preimplantation genetic screening result, a likelihood of viability, or a predicted morphological feature) based on a comparison of the first morpho-kinetic signature and a third morpho-kinetic signature, wherein the third morpho-kinetic signature corresponds to a third embryo that was implanted with the first embryo, and wherein the first embryo was viable and the third embryo was not viable.

For example, the system may train a model with a modified target (=loss) function. This function may use KID embryos (e.g., with known positive or negative classifications. The system may also use KID Unknown embryos (e.g., embryos with partial information such as images of their development but without a label classification such as whether or not the embryo was viable). For example, for two jointly transferred KID Unknown embryos, which ended up in a single live birth, the system will need to receive one high prediction score and one low prediction score. Using these scores, the system may distinguish between the two embryos and determine the embryo that was viable. The system may also penalize (or deemphasize data) with alternative arrangements (e.g., two low scores or two high scores) because in such cases the system cannot identify, which embryo was viable. Through this additional processing step, the system may use KID Unknown embryos in training, which may lead to a better model (as it relies on higher data amounts).

At step 908, process 900 (e.g., via one or more components of system 300 (FIG. 3)) receives an output from the second artificial neural network indicating a viability of the embryo. It is contemplated that the steps or descriptions of FIG. 9 may be used with any other embodiment of this disclosure. In addition, the steps and descriptions described in relation to FIG. 9 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1 and 3-4 could be used to perform one or more of the steps in FIG. 9.

Although the present invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The present techniques will be better understood with reference to the following enumerated embodiments:

1. A method of classifying morphological and morpho-kinetic features in embryos, the method comprising: receiving a first image of a first embryo; labeling the first image with a known morphological or morpho-kinetic feature in the first image; training an artificial neural network to detect the known morphological or morpho-kinetic feature in the first image; receiving a second image of a second embryo; inputting the second image into the trained artificial neural network; and receiving an output from the trained artificial neural network indicating that the second image includes the known morphological or morpho-kinetic feature.

2. A method of classifying morpho-kinetic signatures in embryos, the method comprising: receiving a first morpho-kinetic signature of a first embryo, wherein the first morpho-kinetic signature is a representation of morpho-kinetic events in the first embryo as a function of time; labeling the first morpho-kinetic signature with a known classification; training an artificial neural network to detect the known classification based on the first morpho-kinetic signature; receiving a second morpho-kinetic signature of a second embryo with an unknown classification, wherein the second morpho-kinetic signature is a representation of morpho-kinetic events in the second embryo as a function of time; inputting the second morpho-kinetic signature into the trained artificial neural network; and receiving a prediction from the trained artificial neural network that the second morpho-kinetic signature corresponds to the known classification.

3. A method of generating morpho-kinetic signatures for embryos, the method comprising: receiving a first output from a first artificial neural network indicating that an embryo has a first classification at a first time point; receiving a second output from the first artificial neural network indicating the embryo has a second classification at a second time point; and aggregating the first output and second output to generate a morpho-kinetic signature, wherein the morpho-kinetic signature is a representation of morpho-kinetic events in the embryo as a function of time.

4. A method of predicting viability of embryos based on morpho-kinetic signatures, the method comprising: receiving a plurality of outputs from a first artificial neural network based on a series of images of an embryo; generating a morpho-kinetic signature based on the plurality of outputs, wherein the morpho-kinetic signature is a representation of morpho-kinetic events in the embryo as a function of time; inputting the morpho-kinetic signature into a second artificial neural network; and receiving an output from the second artificial neural network indicating a viability of the embryo.

5. The method of any one of the preceding embodiments, further comprising: receiving a first output from an initial artificial neural network indicating that the first embryo has a first classification at a first time point; receiving a second output from the initial artificial neural network indicating the first embryo has a second classification at a second time point; and aggregating the first output and the second output to generate the first morpho-kinetic signature.

6. The method of any one of the preceding embodiments, further comprising: receiving an annotated image of a training data embryo, wherein the annotated image has a known morphological or morpho-kinetic feature; training the initial artificial neural network to classify images with the known morphological or morpho-kinetic feature in the first classification; receiving a first image of the first embryo; inputting the first image into the initial artificial neural network; and receiving the first output from the initial artificial neural network indicating that the first image includes the known morphological or morpho-kinetic feature.

7. The method of any one of the preceding embodiments, further comprising: receiving known implantation data indicating that the first embryo has a first classification at a first time point; generating a bootstrap label based on the known implantation data, wherein the bootstrap label corresponds to a second classification at a second time point; and aggregating the first classification and the second classification to generate the first morpho-kinetic signature.

8. The method of any one of the preceding embodiments, further comprising: generating the first morpho-kinetic signature of the first embryo based on known implantation data; determining the known classification for the first embryo based on a comparison of the first morpho-kinetic signature and a third morpho-kinetic signature, wherein the third morpho-kinetic signature corresponds to a third embryo that was implanted with the first embryo, and wherein the first embryo was viable and the third embryo was not viable.

9. The method of any one of the preceding embodiments, wherein the known classification corresponds to an implantation quality, a preimplantation genetic screening result, or a predicted morphological feature.

10. The method of any one of the preceding embodiments, wherein a morpho-kinetic event is an appearance of a morphological features in the first embryo and a rate of development for the morphological feature.

11. The method of any one of the preceding embodiments, wherein a morpho-kinetic event is a cell split, a development of a morula, a start of blastulation, a pronuclei appearance, or a pronuclei fading.

12. The method of any one of the preceding embodiments, wherein a morpho-kinetic event is an achievement of a Garner expansion degree.

13. The method of any one of the preceding embodiments, wherein a morpho-kinetic event corresponds to a fragmentation percent at two cells, a fragmentation percent at four cells, a fragmentation percent at eight cells, blastomers symmetry at two cells, blastomers symmetry at four cells, blastomers symmetry at eight cells, inner cell mass quality, trophectoderm quality, cavity shape, cavity area, cavity percentage, and/or zona pellucida thickness.

14. The method of any one of the preceding embodiments, wherein a morpho-kinetic event includes a first appearance of a morphological feature among other morphological features and a clear separation of the morphological feature from the other morphological features.

15. The method of any one of the preceding embodiments, further comprising: labeling the first morpho-kinetic signature with first additional information about the first embryo; training the artificial neural network to detect the known classification based on the first morpho-kinetic signature and the first additional information; receiving second additional information about the second embryo; and inputting the second additional information along with the second morpho-kinetic signature into the trained artificial neural network to receive the prediction.

16. The method of embodiment 15, wherein the first additional information includes clinical data or preimplantation genetic screening data.

17. The method of any one of the preceding embodiments, wherein each morpho-kinetic event of the morpho-kinetic events is represented as a float value in a vector.

18. The method of any one of the preceding embodiments, wherein the first morpho-kinetic signature is based on a series of time-lapse images of the morpho-kinetic events in the first embryo.

19. A tangible, non-transitory, machine-readable medium storing instructions that, when executed by a data processing apparatus, cause the data processing apparatus to perform operations comprising those of any of embodiments 1-18.

20. A system comprising: one or more processors; and memory storing instructions that, when executed by the processors, cause the processors to effectuate operations comprising those of any of embodiments 1-18.

21. A system comprising means for performing any of embodiments 1-18.

What is claimed is:

1. A method of classifying morpho-kinetic signatures in embryos, the method comprising:
receiving, using control circuitry, a first morpho-kinetic signature of a first embryo, wherein the first morpho-kinetic signature is a representation of morpho-kinetic events in the first embryo as a function of time;
labeling, using the control circuitry, the first morpho-kinetic signature with a known classification, wherein the known classification corresponds to a preimplantation genetic screening result or a likelihood of viability;
training, using the control circuitry, an artificial neural network to detect the known classification based on the first morpho-kinetic signature;
receiving, using the control circuitry, a second morpho-kinetic signature of a second embryo with an unknown classification, wherein the second morpho-kinetic signature is a representation of morpho-kinetic events in the second embryo as a function of time;
receiving additional information including a preimplantation genetic diagnosis or a preimplantation genetic screening data;
inputting, using the control circuitry, the additional information along with the second morpho-kinetic signature into the trained artificial neural network; and
receiving, using the control circuitry, a prediction from the trained artificial neural network that the second morpho-kinetic signature corresponds to the known classification, wherein when the known classification is the likelihood of viability that the prediction comprises a prediction score corresponding to the likelihood of viability.

2. The method of claim 1, further comprising:
receiving a first output from an initial artificial neural network indicating that the first embryo has a first classification at a first time point;
receiving a second output from the initial artificial neural network indicating the first embryo has a second classification at a second time point; and
aggregating the first output and the second output to generate the first morpho-kinetic signature.

3. The method of claim 2, further comprising:
receiving an annotated image of a training data embryo, wherein the annotated image has a known morphological or morpho-kinetic feature in the annotated image;
training the initial artificial neural network to classify images with the known morphological or morpho-kinetic feature in the first classification;
receiving a first image of the first embryo;
inputting the first image into the initial artificial neural network; and
receiving, using the control circuitry, the first output from the initial artificial neural network indicating that the first image includes the known morphological or morpho-kinetic feature.

4. The method of claim 1, further comprising:
receiving known implantation data indicating that the first embryo has a first classification at a first time point;
generating a bootstrap label based on the known implantation data, wherein the bootstrap label corresponds to a second classification at a second time point; and
aggregating the first classification and the second classification to generate the first morpho-kinetic signature.

5. The method of claim 1, further comprising:
generating the first morpho-kinetic signature of the first embryo based on known implantation data; and
determining the known classification for the first embryo based on a comparison of the first morpho-kinetic signature and a third morpho-kinetic signature, wherein the third morpho-kinetic signature corresponds to a third embryo that was implanted with the first embryo, and wherein the first embryo was viable and the third embryo was not viable.

6. The method of claim 1, wherein a morpho-kinetic event is an appearance of a morphological features in the first embryo and a rate of development for the morphological feature.

7. The method of claim 1, wherein a morpho-kinetic event is a cell split, a development of a morula, a start of blastulation, a pronuclei appearance, or a pronuclei fading.

8. The method of claim 1, wherein a morpho-kinetic event is an achievement of a Garner expansion degree.

9. The method of claim 1, wherein a morpho-kinetic event corresponds to a fragmentation percent at two cells, a fragmentation percent at four cells, a fragmentation percent at eight cells, blastomers symmetry at two cells, blastomers symmetry at four cells, blastomers symmetry at eight cells, inner cell mass quality, trophectoderm quality, cavity shape, cavity area, cavity percentage, and/or zona pellucida thickness.

10. The method of claim 1, wherein a morpho-kinetic event includes a first appearance of a morphological feature among other morphological features and a clear separation of the morphological feature from the other morphological features.

11. The method of claim 1, wherein each morpho-kinetic event of the morpho-kinetic events is represented as a float value in a vector.

12. The method of claim 1, wherein the first morpho-kinetic signature is based on a series of time-lapse images of the morpho-kinetic events in the first embryo.

13. A system for classifying morpho-kinetic signatures in embryos, the system comprising:
memory configured to store an artificial neural network; and
control circuitry configured to:
receive a first morpho-kinetic signature of a first embryo, wherein the first morpho-kinetic signature is a representation of morpho-kinetic events in the first embryo as a function of time;
label the first morpho-kinetic signature with a known classification, wherein the known classification corresponds to a preimplantation genetic screening result or a likelihood of viability;
train the artificial neural network to detect the known classification based on the first morpho-kinetic signature;
receive a second morpho-kinetic signature of a second embryo with an unknown classification, wherein the second morpho-kinetic signature is a representation of morpho-kinetic events in the second embryo as a function of time;

receiving additional information including a preimplantation genetic diagnosis or a preimplantation genetic screening data;
input the additional information along with the second morpho-kinetic signature into the trained artificial neural network; and
receive a prediction from the trained artificial neural network that the second morpho-kinetic signature corresponds to the known classification, wherein when the known classification is the likelihood of viability that the prediction comprises a prediction score corresponding to the likelihood of viability.

14. The system of claim 13, the control circuitry further configured to:
receive a first output from an initial artificial neural network indicating that the first embryo has a first classification at a first time point;
receive a second output from the initial artificial neural network indicating the first embryo has a second classification at a second time point; and
aggregate the first output and the second output to generate the first morpho-kinetic signature.

15. The system of claim 14, the control circuitry further configured to:
receive an annotated image of a training data embryo, wherein the annotated image has a known morphological or morpho-kinetic feature in the annotated image;
train the initial artificial neural network to classify images with the known morphological or morpho-kinetic feature in the first classification;
receive a first image of the first embryo;
input the first image into the initial artificial neural network; and
receive, using the control circuitry, the first output from the initial artificial neural network indicating that the first image includes the known morphological or morpho-kinetic feature.

16. The system of claim 13, the control circuitry further configured to:
receive known implantation data indicating that the first embryo has a first classification at a first time point;
generate a bootstrap label based on the known implantation data, wherein the bootstrap label corresponds to a second classification at a second time point; and
aggregate the first classification and the second classification to generate the first morpho-kinetic signature.

17. The system of claim 13, the control circuitry further configured to:
generate the first morpho-kinetic signature of the first embryo based on known implantation data; and
determine the known classification for the first embryo based on a comparison of the first morpho-kinetic signature and a third morpho-kinetic signature, wherein the third morpho-kinetic signature corresponds to a third embryo that was implanted with the first embryo, and wherein the first embryo was viable and the third embryo was not viable.

18. The system of claim 13, wherein a morpho-kinetic event is an appearance of a morphological features in the first embryo and a rate of development for the morphological feature.

19. The system of claim 13, wherein a morpho-kinetic event includes a first appearance of a morphological feature among other morphological features and a clear separation of the morphological feature from the other morphological features.

20. The system of claim 13, wherein the first morpho-kinetic signature is based on a series of time-lapse images of the morpho-kinetic events in the first embryo.

21. A non-transitory computer-readable medium for classifying morpho-kinetic signatures in embryos comprising instructions that, when executed by one or more processors, cause operations comprising:
receiving a first morpho-kinetic signature of a first embryo, wherein the first morpho-kinetic signature is a representation of morpho-kinetic events in the first embryo as a function of time;
labeling the first morpho-kinetic signature with a known classification, wherein the known classification corresponds to a preimplantation genetic screening result or a likelihood of viability;
training an artificial neural network to detect the known classification based on the first morpho-kinetic signature;
receiving a second morpho-kinetic signature of a second embryo with an unknown classification, wherein the second morpho-kinetic signature is a representation of morpho-kinetic events in the second embryo as a function of time;
receiving additional information including a preimplantation genetic diagnosis or a preimplantation genetic screening data;
inputting the additional information along with the second morpho-kinetic signature into the trained artificial neural network; and
receiving a prediction from the trained artificial neural network that the second morpho-kinetic signature corresponds to the known classification, wherein when the known classification is the likelihood of viability that the prediction comprises a prediction score corresponding to the likelihood of viability.

22. The computer-readable medium of claim 21, the operations further comprising:
receiving a first output from an initial artificial neural network indicating that the first embryo has a first classification at a first time point;
receiving a second output from the initial artificial neural network indicating the first embryo has a second classification at a second time point; and
aggregating the first output and the second output to generate the first morpho-kinetic signature.

23. The computer-readable medium of claim 22, the operations further comprising:
receiving an annotated image of a training data embryo, wherein the annotated image has a known morphological or morpho-kinetic feature in the annotated image;
training the initial artificial neural network to classify images with the known morphological or morpho-kinetic feature in the first classification;
receiving a first image of the first embryo;
inputting the first image into the initial artificial neural network; and
receiving, using the control circuitry, the first output from the initial artificial neural network indicating that the first image includes the known morphological or morpho-kinetic feature.

24. The computer-readable medium of claim 21, the operations further comprising:
receiving known implantation data indicating that the first embryo has a first classification at a first time point;
generating a bootstrap label based on the known implantation data, wherein the bootstrap label corresponds to a second classification at a second time point; and
aggregating the first classification and the second classification to generate the first morpho-kinetic signature.

25. The computer-readable medium of claim 21, the operations further comprising:
generating the first morpho-kinetic signature of the first embryo based on known implantation data; and
determining the known classification for the first embryo based on a comparison of the first morpho-kinetic signature and a third morpho-kinetic signature, wherein the third morpho-kinetic signature corresponds to a third embryo that was implanted with the first embryo, and wherein the first embryo was viable and the third embryo was not viable.

26. The computer-readable medium of claim 21, wherein a morpho-kinetic event is an appearance of a morphological features in the first embryo and a rate of development for the morphological feature.

27. The computer-readable medium of claim 21, wherein a morpho-kinetic event includes a first appearance of a morphological feature among other morphological features and a clear separation of the morphological feature from the other morphological features.

28. The computer-readable medium of claim 21, wherein the first morpho-kinetic signature is based on a series of time-lapse images of the morpho-kinetic events in the first embryo.

* * * * *